(12) United States Patent
Exalto et al.

(10) Patent No.: US 8,658,863 B2
(45) Date of Patent: Feb. 25, 2014

(54) WHITE KOHLRABI

(75) Inventors: Dirk Willem Exalto, Nieuwe Tonge (NL); Adrianus Johannes Maria Van Den Nieuwenhuizen, Breda (NL)

(73) Assignee: Rijk Zwaan Zaadteelt en Zaadhandel B.V. (NL)

( * ) Notice: Subject to any disclaimer, the term of this patent is extended or adjusted under 35 U.S.C. 154(b) by 35 days.

(21) Appl. No.: 13/036,212

(22) Filed: Feb. 28, 2011

(65) Prior Publication Data

US 2011/0214197 A1 Sep. 1, 2011

Related U.S. Application Data

(63) Continuation-in-part of application No. PCT/EP2009/060346, filed on Aug. 10, 2009.

(30) Foreign Application Priority Data

Aug. 29, 2008 (EP) .................... 08163309

(51) Int. Cl.
*A01H 5/00* (2006.01)
*A01H 5/10* (2006.01)
*A01H 1/00* (2006.01)

(52) U.S. Cl.
USPC .......................... 800/306; 800/260; 435/430

(58) Field of Classification Search
None
See application file for complete search history.

(56) References Cited

PUBLICATIONS

DuFault, J Amer Soc Hort Sci 121(4): 705-710, 1996.*
Cebula, Veg Crops Res Bull 70:101-110, 2009.*
International Seeds Processing GMBH: *Brassica oleracea* Aceph. Gongylodes, Kohlrabi, Knaufs Fruhweiss (2006), Fig. 1, Retrieved from URL:http://www.isp-quedlinburg.de/english/gemuese_2006_english.htm Retrieved Dec. 22, 2008.
International Seeds Processing GMBH: 443230, *Brassica oleracea* Aceph. Gongylodes, Kohlrabi, Delikatess, Weisser (2006) Fig. 1, Retrieved from URL:http://www.isp-quedlinburg.de/english/gemuese_2006_english.htm Retrieved Dec. 22, 2008.
Blumenshop.DE: Kohlrabi Delikatess Weisser Fruher Oberkohlrabi (2007), Fig. 1, Retrieved from URL:http://www.blumensamen-shop:de/bilder/127-Kohlrabi-Frk-60.jpg Retrieved Dec. 22, 2008.
Beata Jankowska, The Occurrence Of Some Lepidoptera Pests On Different Cabbage Vegetables, J. of Plant Protection Research (2006) vol. 46, No. 2, p. 181-190.
Gy. Mandy, White Kohlrabi Of Szentes, Acta Agronomica Academiae Scientiarum Hungaricae (1971) vol. 20, No. 1-2, p. 165-166.
International Seeds Processing GMBH: *Brassica oleracea* Aceph. Gongylodes, Kohlrabi, Knaufs Fruhweiss (2006), Fig. 1.
International Seeds Processing GMBH: 443230, *Brassica oleracea* Aceph. Gongylodes, Kohlrabi, Delikatess, Weisser (2006), Fig. 1.
Blumenshop.DE: Kohlrabi Delikatess Weisser Fruher Oberkohlrabi (2007), Fig. 1.

* cited by examiner

*Primary Examiner* — Elizabeth McElwain
(74) *Attorney, Agent, or Firm* — Vedder Price P.C.; Thomas J. Kowalski; Deborah L. Lu (57) ABSTRACT

The invention relates to a kohlrabi plant carrying a genetic trait that leads to petioles, stems and bulb having an extra white color at harvest stage as compared to the petioles, stems and bulb of a kohlrabi plant not carrying the said genetic trait. The extra white color may be a color graded in the white group for example the color 155 A or B or C or NN 155 A or B or C or D and in the greed-green group for example the colors 190 D or 191 D or 192 D or 193 D according to The RHS Color Chart, fifth edition. The plant may be obtainable by crossing a first kohlrabi parent plant with a second kohlrabi parent plant, wherein one of the parents is a plant grown from seeds of which a representative sample was deposited with the NCIMB under deposit accession number NCIMB 41530 or a progeny plant thereof and selecting for plants which have the genetic trait that leads to an extra white color of the petioles, stems and bulb as compared to the petioles, stems and bulb of a plant not carrying the genetic trait.

12 Claims, 3 Drawing Sheets
(3 of 3 Drawing Sheet(s) Filed in Color)

extra white light green

FIG. 1 extra white light green

FIG. 2 extra white light green

FIG. 3

WHITE KOHLRABI

RELATED APPLICATIONS AND INCORPORATION BY REFERENCE

This application is a continuation-in-part application of international patent application Serial No. PCT/EP2009/060346 filed 10 Aug. 2009, which published as PCT Publication No. WO 2010/023093 on 4 Mar. 2010, which claims benefit of European patent application Serial No. 08163309.1 filed 29 Aug. 2008.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to kohlrabi plants that carry a new colour trait. The invention further relates to progeny and propagation material of these plants.

BACKGROUND OF THE INVENTION

Kohlrabi is a vegetable of the species *Brassica oleracea* spp Gongylodes Group. It is grown for its bulb (stem tuber), which may used as a cooked vegetable, but is also used in soups or eaten raw in salads. The bulb of kohlrabi is usually light green with sometimes shades of purple.

In the vegetable market there is always a desire for vegetables that are different in appearance from the existing vegetables. The consumer prefers variation in the colours of vegetables.

It is therefore an object of the invention to provide kohlrabi with a colour that differs from the existing kohlrabi plants.

Citation or identification of any document in this application is not an admission that such document is available as prior art to the present invention.

SUMMARY OF THE INVENTION

According to the invention a mutant kohlrabi was developed that has a very white stem, very white petioles and a very white bulb. This trait will be called herein the "extra white trait". "Extra white" in this respect means having a colour that is graded in the white group with the colour range 155 A or B or C and NN 155 A or B or C or D or in the greyed-green group the colour range 190 D or 191 D or 192 D or 193 D according to the RHS Colour Chart of the Royal Horticultural Society, fifth edition. The colour of normal kohlrabi has a colour in the range of the yellow-green group colours 149 A or B or C or D and 150 C and D according to the same color chart. The RHS Colour Chart is the standard reference for plant colour identification.

The extra white colour trait is caused by a single dominant gene. Thus, hybrids having the trait can be made when one of the parents is homozygous for this trait. The trait can be introduced in all types of kohlrabi plants.

The kohlrabi plants of the invention are obtainable by crossing a first kohlrabi parent plant with a second kohlrabi parent plant, wherein one of the parents is a plant grown from seeds of which a representative sample was deposited with the NCIMB under deposit accession number NCIMB 41530 or a progeny plant thereof and selecting for plants which have the genetic trait that leads to an extra white colour of the petioles, stems and bulb as compared to the petioles, stems and bulb of a plant not carrying the genetic trait.

The invention furthermore relates to a kohlrabi bulb of a plant of the invention. The kohlrabi bulb is usually sold as a vegetable either with or without leafs but without the roots. The invention relates to both embodiments.

The invention further relates to seed of the kohlrabi plant of the invention and to parts of the plant that are suitable for sexual reproduction. Such parts are for example selected from the group consisting of microspores, pollen, ovaries, ovules, embryo sacs and egg cells. In addition the invention relates to parts of the plant that are suitable for vegetative reproduction, in particular cuttings, roots, stems, cells, protoplasts.

According to a further aspect thereof the invention provides a tissue culture of the extra white kohlrabi plant. The tissue culture comprises regenerable cells. Such tissue culture can be derived from leaves, pollen, embryos, cotyledon, hypocotyls, meristematic cells, roots, root tips, anthers, flowers, seeds and stems.

According to another aspect of the invention kohlrabi plants are provided that have all of the morphological and physiological characteristics of kohlrabi plants of the invention, representative seed of which having been deposited under NCIMB Accession number NCIMB 41530, which plants are grown from seeds of the plant of the invention or regenerated from parts thereof, or from a tissue culture.

The invention also relates to progeny of the kohlrabi plant of the invention. Such progeny can be produced by sexual or vegetative reproduction of a plant of the invention or a progeny plant thereof. The regenerated plant has all of the relevant morphological and physiological characteristics of the claimed plant, representative seed of which having been deposited under NCIMB Accession number NCIMB 41530. This means that such progeny has the same characteristics as claimed for the kohlrabi plant of the invention, i.e. the extra white trait. In addition to this, the plant may be modified in one or more other characteristics. Such additional modifications are for example effected by mutagenesis or by transformation with a transgene.

The invention furthermore relates to hybrid seed and to a method of producing hybrid seed comprising crossing a first parent plant with a second parent plant and harvesting the resultant hybrid seed, wherein said first parent plant or said second parent plant is the plant as claimed.

Furthermore, the invention provides small plants or parts thereof that may be suitable for consumption such as sprouts, cress and cotyledons. The invention also relates to food products that comprise such small plants or parts of the kohlrabi bulb.

According to a further aspect thereof the invention provides a method of producing a cultivar having the characteristics of a plant of the invention, which method comprises:
 a) crossing a mother plant with a father plant to produce a hybrid seed;
 b) growing said hybrid seed to produce a hybrid plant;
 c) selfing said hybrid seed to produce F2 progeny seed;
 d) selecting said F2 plants for having the extra white characteristics of the invention; and
 e) optionally repeating steps c) and d),
wherein at least either the mother plant or the father plant is a plant of the invention or a progeny plant thereof.

It is clear that the parent that provides the trait of the invention is not necessarily a plant grown directly from the deposited seeds. The parent can also be a progeny plant from the seed or a progeny plant from seeds that are identified to have the trait of the invention by other means.

Seeds of the new "extra white" kohlrabi (*Brassica oleracea* ss *gongylodes*) were deposited on 7 Dec. 2007 with NCIMB Ltd., Ferguson Building, Craibstone Estate, Bucksburn, Aberdeen, AB21 9YA Scotland, UK and given the accession number NCIMB 41530.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

The Deposits with NCIMB Ltd., under deposit accession number NCIMB 41530 were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

The invention is illustrated in the following figures.

In all figures the shaded parts in the corresponding drawings of the plant of the invention are "extra white", where these parts are light green in the known kohlrabi.

DETAILED DESCRIPTION OF THE INVENTION

Introgression

Figure 1:
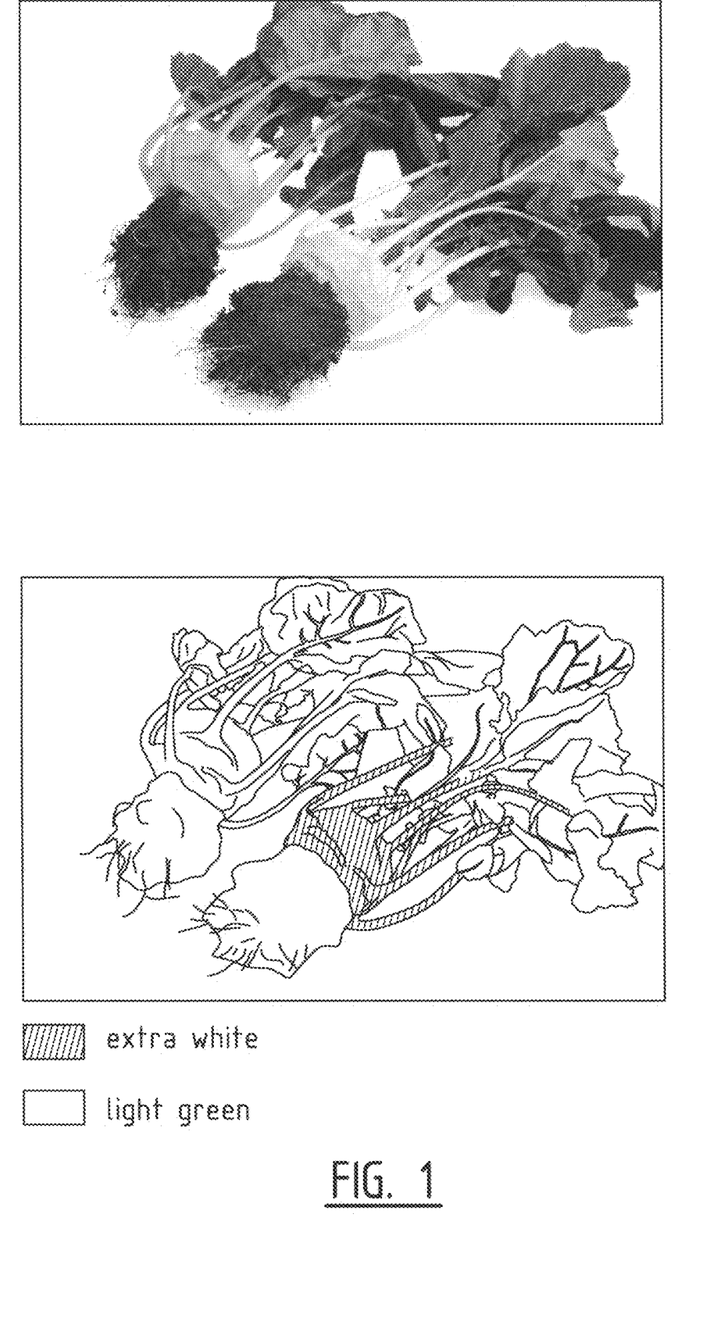
FIG. 1: A comparison between a normal kohlrabi plant (left) and a kohlrabi plant of the invention (right).
Figure 2:
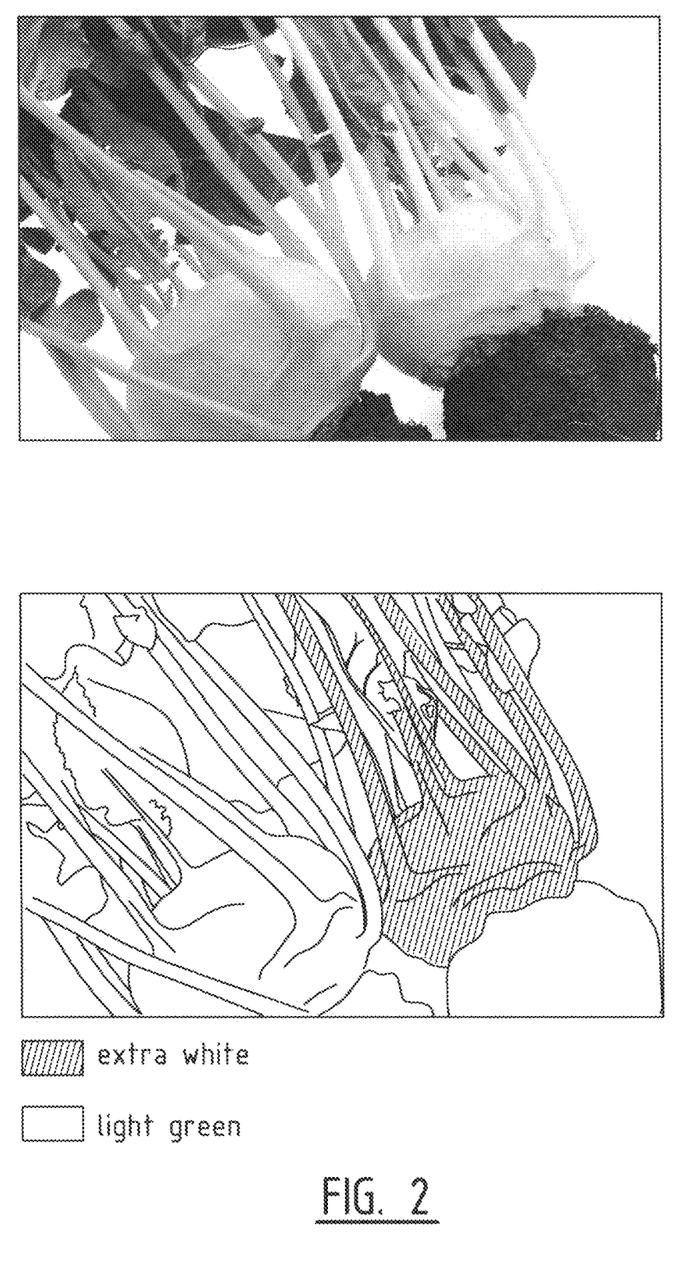
FIG. 2: A close-up of the plants shown in FIG. 1.
Figure 3:
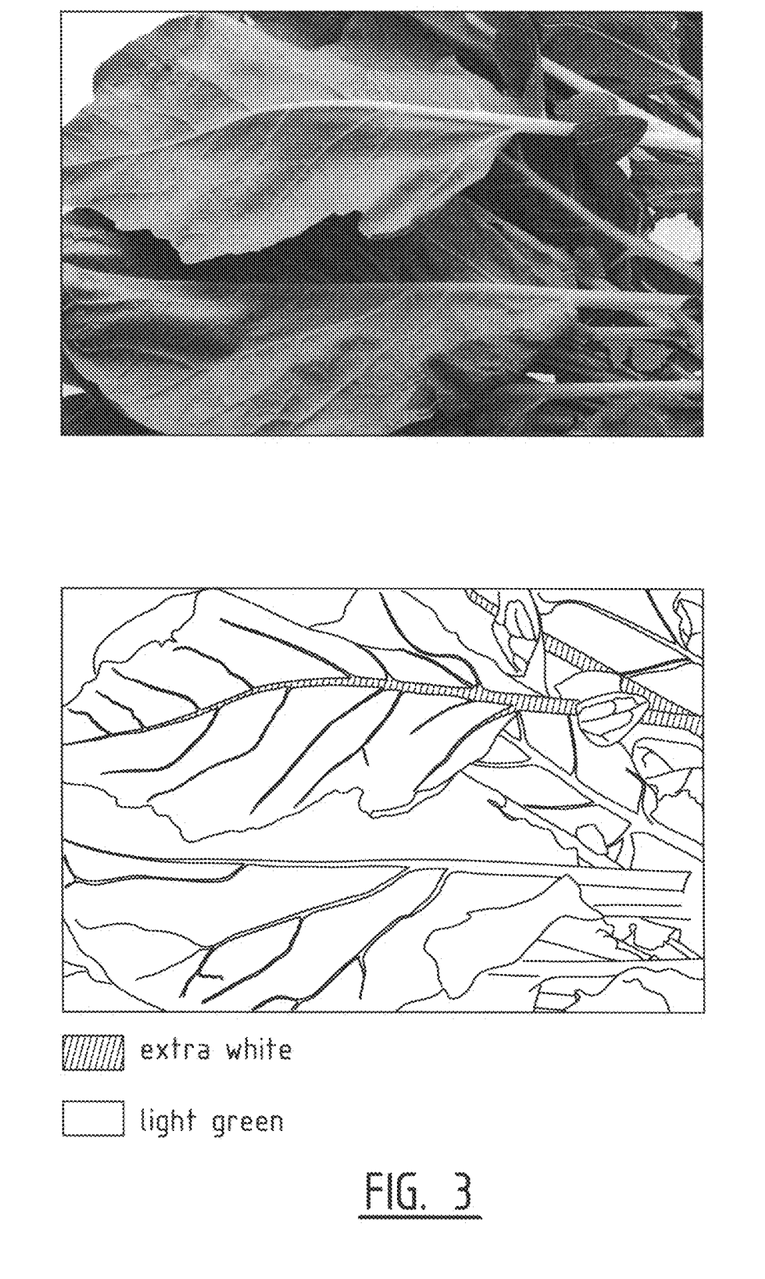
FIG. 3: A close-up of the leaves of the plants shown in FIG. 1.

In an embodiment, the trait is introgressed from a plant grown from seed that was deposited with the NCIMB under accession number NCIMB 41530 or a progeny plant thereof.

"Introgression" as used herein is intended to mean introduction of a trait into a plant not carrying the trait by means of crossing and selection.

It is noted that if the selection criterion or criteria is or are clearly defined, the skilled person will be able to identify the descendants that carry the trait in any further generation. For the trait of the invention descendants from a cross between a plant not carrying the extra white trait and a plant carrying the extra white trait as found in plants of which representative seeds was deposited under accession number NCIMB 41530 can be identified by growing F2 plants from seeds that are the result from the initial cross and a selfing step, selecting plants exhibiting the extra white trait, i.e. that produce leaves as plants having the extra white trait, e.g., that produce leaves as plants grown from seed deposited under deposit accession number NCIMB 41530 (as such seed is representative of seeds of plants that exhibit the extra white trait).

Crossing

In an embodiment, the invention relates to kohlrabi obtainable by crossing a first kohlrabi parent plant with a second kohlrabi parent plant that has the extra white trait as found in plants of which representative seed was deposited under deposit accession number NCIMB 41530 to obtain an F1, subsequently selfing plants of the F1 to obtain an F2 and selecting plants from the F2 that have the extra white trait as plants of the invention. The extra white trait is caused by a single dominant gene.

Selection of kohlrabi for breeding therefore can also be independent of the phenotype of a plant and instead can be based on genetic investigations. For example, one can utilize a suitable genetic marker which is closely genetically linked to a trait of interest—the extra white trait in this instance, e.g., as identified using seed deposited under deposit accession number NCIMB 41530. These markers can be used to identify the presence of the trait in the offspring of a particular cross (e.g., two heterozygous plants that carry the genetic information for the extra white trait but do not have that phenotype because it is recessive and they are not homozygous therefor), and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Methods for marker assisted selection are of particular utility in the case of recessive traits and variable phenotypes, or where conventional assays may be more expensive, time consuming or otherwise disadvantageous, and types of genetic markers which could be used in accordance with the invention include, but are not necessarily limited to, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs), and Single Nucleotide Polymorphisms (SNPs). Reference is made to U.S. Pat. No. 7,705,206, for documents and a discussion relating to the foregoing methods; and, U.S. Pat. No. 7,705,206, and the documents cited therein, including as to the foregoing methods, are hereby incorporated herein by reference consistent with the above RELATED APPLICATIONS & INCORPORATION BY REFERENCE section.

In an embodiment the second kohlrabi parent plant is a plant grown from the deposited seeds.

In an embodiment the second kohlrabi parent plant is a progeny plant of a plant grown from the deposited seeds.

In an embodiment the second kohlrabi parent plant is a plant having the genetic information that encodes the extra white trait phenotype.

In an embodiment this genetic information is substantially identical to the genetic information that encodes the extra white trait as found in plants of which representative seeds were deposited under deposit accession number NCIMB 41530, in particular plants grown from seeds as deposited under deposit accession number 41530 (wherein "substantially identical" is identical to the genetic information in the seeds deposited under NCIMB 41530, or so similar to the genetic information in the seeds deposited under NCIMB 41530 at the locus or gene that gives rise to expression of the extra white trait phenotype in the seeds deposited under deposit number 41530 such that the sample also has the extra white trait, e.g., a sample can be "substantially identical" in its genome to seeds deposited under deposit number 41530 because it is different than the genome of seeds deposited under deposit number 41530 due to the degeneracy of the genetic code).

In an embodiment, the invention thus relates to a kohlrabi, showing the extra white trait, which plant is obtainable by:
(a) growing plants representative seed of which was deposited under NCIMB number 41530;
(b) crossing a plant from step a) with a kohlrabi that does not have the extra white trait to obtain an F1 population;
(c) selfing plants from the F1 to obtain a F2 population; and
(d) identifying plants showing the extra white trait in the F2 population as kohlrabi.

In the method described above steps c) and d) can be repeated one or more times by selfing an Fn population to obtain an Fn+1 population and identifying plants showing the extra white trait in the Fn+1 population as kohlrabi.

Genotype

The extra white trait is phenotypically visible because plants have a very white stem, very white petioles and a very white bulb. The trait is however caused by the plant's genotype. The genotype as far as it concerns the extra white trait is the same as or substantially similar or identical to genotype as found in the deposited seeds. On a nucleic acid molecule basis, this can mean a first nucleic acid molecule having at least 95, 96, 97, 98 or 99 percent identity with a second nucleic molecule, wherein the second acid molecule is of a herein identified or exemplified or deposited plant, plant part, seed, cell or the like, and the expression of both the first and second nucleic acid molecules in a kohlrabi results in the phenotype of the extra white trait. The part of the genotype of a kohlrabi that causes the extra white trait will be called herein the "genetic information that encodes the extra white trait". Presence of this genetic information is phenotypically visible and plants having this genetic information can thus be selected on the basis of this phenotypic expression of the underlying gene or genes.

As used herein "genetic information" is intended to mean the portion of the genome, e.g. gene or genes, that are responsible for the formation of a very white stem, very white petioles and a very white bulb; which portion of the genome can be detected in the genome, e.g. by detecting polymorphisms in the genome of "extra white trait" plants of which representative seed was deposited under deposit accession number NCIMB 41530, and that portion of the genome, particularly the portion that gives rise to expression of the "extra white trait" can thus be isolated from the genome and can be an isolated nucleic acid molecule encoding the extra white trait (which when introduced into the genome of a regenerable cell of a kohlrabi that does not carry this genotype and when in the cell operably linked to and under the control of a suitable promoter, gives rise to the expression of the "extra white trait" in a kohlrabi regenerated from a tissue culture of such regenerable cells into which the isolated nucleic acid molecule has been introduced and is present in the cells operably linked to and under the control of a suitable promoter).

The presence of the genetic information that is responsible for the extra white trait of the invention in the genome of a plant that shows a extra white trait characteristic can be determined with the following test: The plant to be tested should be or should be made to be homozygous for the genetic information responsible for the extra white trait. The skilled person knows how to obtain a plant that is homozygous for the trait to be tested, e.g., via selfing or self mating or self crossing. This homozygous plant is then crossed with a tester plant that carries the genetic information that is responsible for the trait of the invention in homozygous condition. If the plant to be tested has a extra white trait as a result of the same genetic information that is responsible for the trait of the invention, all progeny plants of this first cross and successive generations will express the trait. If the extra white trait characteristic of the plant to be tested is the result of a different part of the genome, e.g. another gene or locus, segregation will occur. The tester plant can be any plant that carries the genetic information of the invention in homozygous condition, such as plants of which representative seed was deposited under accession number NCIMB 41530 or plants directly grown from the deposited seeds or progeny thereof that has retained the trait.

In an embodiment of the invention a kohlrabi is provided that comprises the extra white trait and thus when crossed with a tester plant, that comprises the extra white trait of the invention and representative seed of which as deposited with the NCIMB under accession numbers a NCIMB 41530, or a progeny plant thereof that comprises the extra white trait comprised in kohlrabi representative seed of which was deposited with the NCIMB under accession number NCIMB 41530 or a plant derived therefrom and comprising the extra white trait, plants of the first generation progeny (F1) of said cross show a 1:0 segregation for the extra white trait. In both the tester plant and the plant of the invention the extra white trait is present in homozygous condition. Plants of the second and further generations, if obtained by selfing also show a 1:0 segregation for the extra white trait. The tester plant can be a plant of which representative seed was deposited with the NCIMB under accession number NCIMB 41530. When the genetic information responsible for the extra white trait as contained in the deposit is present in a plant, the plant is a plant of the invention (and seeds therefrom are seeds of the invention, plant parts thereof are plant parts of the invention, etc.).

The extra white trait of the invention has a genetic basis in the genome of the kohlrabi. With the above described cross with a tester plant, plants can be identified as being plants of the invention.

The extra white trait is independent of other traits of a kohlrabi. The trait can thus occur in kohlrabi that are completely different in all their other characteristics, for example in different kohlrabi varieties.

The deposited kohlrabi seeds contain in their genome the genetic information that encodes the extra white trait. The deposited seeds are thus a source for the genetic information that leads to the trait. The skilled person is capable of introducing the trait into any other kohlrabi he desires.

In one embodiment, the source from which the genetic information is acquired is formed by plants grown from the deposited seeds or sexual or vegetative descendants therefrom.

It is clear, however, that a parent that provides the trait of the invention is not necessarily a plant grown directly from the deposited seeds. For example, the parent can also be a progeny plant from the seed or a progeny plant from seeds that are identified to have or to have acquired the trait of the invention by other means.

Introducing Trait or Additional Traits

In an embodiment, the invention relates to kohlrabi that carry the trait of the invention and have acquired said trait by introduction of the genetic information that is responsible for the trait from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits that can be introduced by backcrossing, useful traits can be introduced directly into a extra white kohlrabi of the invention, by genetic transformation techniques; and, such kohlrabi that have additional genetic information introduced into the genome or that express additional traits by having the DNA coding therefor introduced into the genome via transformation techniques, are within the ambit of the invention, as well as uses of such plants, and the making of such plants.

Genetic transformation may therefore be used to insert a selected transgene into the kohlrabi of the invention or may, alternatively, be used for the preparation of transgenes which can be introduced by backcrossing. Methods for the transformation of plants, including kohlrabi, are well known to those of skill in the art.

Vectors used for the transformation of kohlrabi cells are not limited so long as the vector can express an inserted DNA in the cells. For example, vectors comprising promoters for constitutive gene expression in kohlrabi cells (e.g., cauliflower mosaic virus 35S promoter) and promoters inducible by exogenous stimuli can be used. Examples of suitable vectors include pBI binary vector. The "kohlrabi cell" into which the vector is to be introduced includes various forms of kohlrabi cells, such as cultured cell suspensions, protoplasts, leaf sections, and callus. A vector can be introduced into kohlrabi cells by known methods, such as the polyethylene glycol method, polycation method, electroporation, *Agrobacterium*-mediated transfer, particle bombardment and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target kohlrabi cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including the kohlrabi of the invention.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations. Moreover, advances in vectors for *Agrobacterium*-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, *Agrobacterium* containing both armed and disarmed Ti genes can be used for transformation. In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells, including kohlrabi cells, is well known in the art (See, e.g., U.S. Pat. Nos. 7,250,560 and 5,563,055).

Transformation of plant protoplasts also can be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for extra white trait gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins from kohlrabi (psaD, psaF, psaE, PC, FNR, atpC, atpD, cab, rbcS) (see U.S. Pat. No. 7,161,061), the CAB-1 promoter from kohlrabi (see U.S. Pat. No. 7,663,027), the promoter from maize prolamin seed storage protein (see U.S. Pat No. 7,119,255), and other plant DNA virus promoters known to express in plant cells. A variety of plant gene promoters that are regulated in response to environmental, hormonal, chemical, and/or developmental signals can be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wunl, or (5) chemicals such as methyl jasmonate, salicylic acid, or Safener. It may also be advantageous to employ organ-specific promoters.

Exemplary nucleic acids which may be introduced to the extra white trait kohlrabi of this invention include, for example, DNA sequences or genes from another species, or even genes or sequences which originate with or are present in kohlrabi species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into kohlrabi according to the invention. Non-limiting examples of particular genes and corresponding phenotypes one may choose to introduce into kohlrabi include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences can affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat No. 7,576,262, "Modified gene-silencing RNA and uses thereof.")

U.S. Pat. Nos. 7,230,158, 7,122,720, 7,081,363, 6,734, 341, 6,503,732, 6,392,121, 6,087,560, 5,981,181, 5,977,060, 5,608,146, 5,516,667, each of which, and all documents cited therein are hereby incorporated herein by reference, consistent with the above RELATED APPLICATIONS & INCORPORATION BY REFERENCE section, are additionally cited as examples of U.S. Patents that may concern transformed kohlrabi and/or methods of transforming kohlrabi or kohlrabi cells, and techniques from these US Patents, as well as promoters, vectors, etc., may be employed in the practice of this invention to introduce exogenous nucleic acid sequence(s) into the extra white trait kohlrabi (or cells thereof) of the invention, and exemplify some exogenous nucleic acid sequence(s) which can be introduced into the kohlrabi (or cells thereof) of the invention, as well as techniques, promoters, vectors etc., to thereby obtain further extra white trait kohlrabi, plant parts and cells, seeds, other propagation material harvestable parts of these plants, etc. of the invention, e.g. tissue culture, including a cell or protoplast, such as an embryo, meristem, cotyledon, pollen, leaf, anther, root, root tip, pistil, flower, seed or stalk.

Propagation Material

The invention further relates to propagation material for producing plants of the invention. Such propagation material comprises inter alia seeds of the claimed plant and parts of the plant that are suitable for sexual reproduction. Such parts are for example selected from the group consisting of seeds, microspores, pollen, ovaries, ovules, embryo sacs and egg cells. In addition, the invention relates to propagation material comprising parts of the plant that are suitable for vegetative reproduction, for example cuttings, roots, stems, cells, protoplasts.

According to a further aspect thereof the propagation material of the invention comprises a tissue culture of the claimed plant. The tissue culture comprises regenerable cells. Such tissue culture can be derived from leaves, pollen, embryos, cotyledon, hypocotyls, meristematic cells, roots, root tips, anthers, flowers, seeds and stems.

Morphological and Physiological Characteristics

According to another aspect of the invention kohlrabi plants are provided that have all of the morphological and physiological characteristics corresponding to the extra white trait of kohlrabi of the invention, representative seed of which having been deposited under NCIMB Accession No. NCIMB 41530, which plants are grown from seeds of a plant of the invention or regenerated from parts thereof, or from a tissue culture. Plants of the invention should have the morphological and physiological characteristics that correspond with the extra white trait but do not necessarily have all the other characteristics of plants of the deposited seeds. The trait is broadly transferrable over multiple kohlrabi types and varieties.

Progeny

The invention also relates to progeny of the kohlrabi of the invention. Such progeny can be produced by sexual or vegetative reproduction of a plant of the invention or a progeny plant thereof. The regenerated progeny plant shows the extra white trait characteristic in the same or a similar way as the plant, of which representative seed was deposited (NCIMN 41530). This means that such progeny has the same characteristics as claimed for the kohlrabi of the invention. In addition to this, the plant may be modified in one or more other characteristics. Such additional modifications are for example effected by mutagenesis or by transformation with a transgene or cisgene. Alternatively, modifications in characteristics other than the extra white trait can be introduced by introducing the extra white trait in a different background.

As used herein the word "progeny" is intended to mean the offspring or the first and all further descendants from a cross with a plant of the invention that shows extra white trait characteristics. Progeny of the invention are descendants of any cross with a plant of the invention that carries the extra white trait.

"Progeny" also encompasses plants that carry the trait of the invention which are obtained from other plants of the invention by vegetative propagation or multiplication.

In one embodiment, the progeny plant has all of the morphological and physiological characteristics of the claimed plant in respect of the extra white trait, representative seed of which having been deposited under accession number NCIMB 41530. Such progeny has the same extra white trait characteristics as claimed for the plant of the invention and may be modified in one or more other characteristics.

Cells, Plants, Seed, Germplasm and Leaves

The invention further relates to cells of kohlrabi as described herein. The cells comprise the genetic information that leads to the extra white trait as described herein. Suitably, this genetic information is substantially identical, preferably completely identical to the genetic information encoding the extra white trait of plants that have all of the morphological and physiological characteristics pertaining to the extra white trait of kohlrabi of the invention, representative seed of which having been deposited under accession number NCIMB 41530. Preferably, the cell of the invention is part of a plant or plant part, but the cell may also be in isolated form.

In an embodiment the plants of the invention are plants grown from seeds having the deposit accession number NCIMB 41530.

In an embodiment the plants of the invention are progeny plants of plants grown from seeds having the deposit accession number NCIMB 41530 that carry the extra white trait.

In an embodiment the plants of the invention are plants that carry in their genome the genetic information that is responsible for the extra white trait by causing the plant to form significantly more leaves than a plant not having the said genetic information in its genome.

The invention, furthermore, relates to hybrid seed and to a method of producing hybrid seed comprising crossing a first parent plant with a second parent plant and harvesting the resultant hybrid seed. In order for the hybrid seed to express the trait of the invention, both parent plants need to be homozygous for the extra white trait but not necessarily uniform for other traits.

The invention also relates to the germplasm of plants of the invention. The germplasm is constituted by all inherited characteristics of an organism and according to the invention encompasses at least the extra white trait of the invention.

The invention also relates to the kohlrabi leaves that are produced by the plants of the invention and marketed as vegetables, either as fresh vegetables or processed, i.e. cooked, and optionally frozen.

The invention further relates to a container comprising one or more plants of the invention in a growth substrate for harvest of leaves from the plant in a domestic environment. This way the consumer can pick very fresh leaves for use in salads. More generally, the invention includes one or more plants of the invention wherein the plant is in a ready-to-harvest condition, including with the consumer picking his own, and further including a container comprising one or more of these plants.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

In order to obtain plants of the invention, the following crosses were made. The progeny was selected for the presence of very white petioles, stems and bulb.

P23, P173, BE392 and KO2411 are all kohlrabi breeding lines of Rijk Zwaan. Korist is a commercial hybrid of Bejo Seeds.

In cross 31281 F1 one very white plant was found (03.70558). This plant is selfed to get a F2 population (05.91695). From this plant also DH plants were produced via microspore culture.

The F2 population segregated in 93 white to 24 normal and the 38 DH lines segregated in 15 white to 23 normal green. These segregation data show that a single dominant gene is responsible for the extra white characteristic.

The kohlrabi of the invention is a normal kohlrabi in shape and behaviour. The colour of the leaves is normal green, blue green, grey green but the colour of the petioles is extreme white due to absence of chlorophyll. The rest of the characteristics are similar to regular kohlrabi. The specific character can be introduced in all types of kohlrabi that are usable for the different growing conditions and horticultural practices.

The invention is further described by the following numbered paragraphs:

1. Kohlrabi plant carrying a genetic trait that leads to petioles, stems and bulb having an extra white colour at harvest stage as compared to the petioles, stems and bulb of a kohlrabi plant not carrying the said genetic trait.

2. Kohlrabi plant as in paragraph 1, wherein the genetic trait is already visible in a young plant stage, in particular about two to three months after sowing directly after transplanting.

3. Kohlrabi plant as in paragraph 1 or 2, wherein the extra white colour is a colour graded in the white group for example the colour 155 A or B or C or NN 155 A or B or C or D and in the greed-green group for example the colours 190 D or 191 D or 192 D or 193 D according to The RHS Colour Chart, fifth edition.

4. Kohlrabi plant as in paragraph 1, 2 or 3, obtainable by crossing a first kohlrabi parent plant with a second kohlrabi parent plant, wherein one of the parents is a plant grown from seeds of which a representative sample was deposited with the NCIMB under deposit accession number NCIMB 41530 or a progeny plant thereof and selecting for plants which have the genetic trait that leads to an extra white colour of the petioles, stems and bulb as compared to the petioles, stems and bulb of a plant not carrying the genetic trait.

5. Kohlrabi bulb of a plant as in any one of the paragraphs 1-4.

6. Propagation material suitable for producing a plant as in any one of the paragraphs 1-4, wherein the propagation material is selected from seeds, parts of the plant that are suitable for sexual reproduction, in particular microspores, pollen, ovaries, ovules, embryo sacs and egg cells, parts of the plant that are suitable for vegetative reproduction, in particular cuttings, roots, stems, cells and protoplasts, tissue cultures of regenerable cells, parts of the plant that are suitable for preparing tissue cultures, in particular leaves, pollen, embryos, cotyledon, hypocotyls, meristematic cells, roots, root tips, anthers, flowers, seeds and stems, wherein the plant produced from the propagation material carries the genetic trait that leads to extra white petioles, stems and bulb as compared to the petioles, stems and bulb of a plant not carrying the genetic trait.

7. Doubled haploid kohlrabi plant, which is homozygous for the genetic trait that leads to extra white petioles, stems and bulb as compared to the petioles, stems and bulb of a plant not carrying the genetic trait.

8. Hybrid kohlrabi plant having extra white petioles, stems and bulb, obtainable by crossing a plant grown from seeds of which a representative sample was deposited with the NCIMB under deposit accession number NCIMB 41530 or a progeny plant thereof with another plant and selecting for plants which have the genetic trait that leads to an extra white colour of the petioles, stems and bulb as compared to the petioles, stems and bulb of a plant not carrying the genetic trait.

9. Small kohlrabi plant as in any one of the paragraphs 1-8, or part thereof, which small plant or part thereof is selected from sprouts, cress or cotyledons.

10. Food product, comprising the bulb of a kohlrabi plant as in any one of the paragraphs 1-8 or parts thereof.

11. Food product, comprising small kohlrabi plants as in any one of the paragraphs 1-8 or parts thereof, in particular sprouts, cress or cotyledons.

12. Method of producing a cultivar having the characteristics of a plant as in any one of the paragraphs 1-8, which method comprises:

a) crossing a mother plant with a father plant to produce a hybrid seed;

b) growing said hybrid seed to produce a hybrid plant;

c) selfing said hybrid seed to produce F2 progeny seed;

d) selecting said F2 plants for having the extra white characteristics of the invention; and e) optionally repeating steps c) and d), wherein either the mother plant or the father plant is a plant as in any one of the paragraphs 1-8 or a progeny plant thereof.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A kohlrabi plant having a phenotypic and genetic trait that leads to petioles, stems and bulb having an extra white color at harvest stage as compared to the petioles, stems and bulb of a kohlrabi plant not carrying the said phenotypic and genetic trait, wherein the genetic information that encodes the extra white trait is as found in the genome of plants grown from seeds with deposit accession account number NCIMB 41530.

2. The kohlrabi plant as claimed in claim 1, wherein the genetic trait is already visible in a young plant stage, in particular about two to three months after sowing directly after transplanting.

3. The kohlrabi plant as claimed in claim 1, wherein the extra white color is a color graded in the white group for example the color 155 A or B or C or NN 155 A or B or C or D and in the greed-green group for example the colors 190 D or 191 D or 192 D or 193 D according to The RHS Colour Chart, fifth edition.

4. The kohlrabi plant as claimed in claim 1, obtainable by crossing a first kohlrabi parent plant with a second kohlrabi parent plant, wherein one of the parents is a plant grown from seeds of which a representative sample was deposited with the NCIMB under deposit accession number NCIMB 41530 or a progeny plant thereof and selecting for plants which have the genetic trait that leads to an extra white color of the petioles, stems and bulb as compared to the petioles, stems and bulb of a plant not carrying the genetic trait.

5. A kohlrabi bulb of a plant as claimed in claim 1.

6. Propagation material suitable for producing a plant as claimed in claim 1, wherein the propagation material is selected from seeds, parts of the plant that are suitable for sexual reproduction, in particular microspores, pollen, ovaries, ovules, embryo sacs and egg cells, parts of the plant that are suitable for vegetative reproduction, in particular cuttings, roots, stems, cells and protoplasts, tissue cultures of regenerable cells, parts of the plant that are suitable for preparing tissue cultures, in particular leaves, pollen, embryos, cotyledon, hypocotyls, meristematic cells, roots, root tips, anthers, flowers, seeds and stems, wherein the plant produced from the propagation material carries the genetic trait that leads to extra white petioles, stems and bulb as compared to the petioles, stems and bulb of a plant not carrying the genetic trait.

7. A doubled haploid kohlrabi plant, which is homozygous for a phenotypic and genetic trait that leads to extra white petioles, stems and bulb as compared to the petioles, stems and bulb of a plant not carrying the phenotypic and genetic trait, wherein the genetic information that encodes the extra white petioles, stems and bulb is as found in the genome of plants grown from seeds with deposit accession account number NCIMB 41530.

8. A hybrid kohlrabi plant having extra white petioles, stems and bulb, obtainable by crossing a plant grown from seeds of which a representative sample was deposited with the NCIMB under deposit accession number NCIMB 41530 or a progeny plant thereof with another plant and selecting for plants which have the genetic trait that leads to an extra white colour of the petioles, stems and bulb as compared to the petioles, stems and bulb of a plant not carrying the genetic trait.

9. A small kohlrabi plant as claimed in claim 1, or part thereof, which small plant or part thereof is selected from sprouts, cress or cotyledons.

10. A food product, comprising the bulb of a kohlrabi plant as claimed in claim 5 or parts thereof.

11. A food product, comprising small kohlrabi plants as claimed in claim 1 or parts thereof, in particular sprouts, cress or cotyledons.

12. A method of producing a cultivar having the characteristics of a plant as claimed in claim 1, which method comprises: a) crossing a mother plant with a father plant to produce a hybrid seed; b) growing said hybrid seed to produce a hybrid plant; c) selfing said hybrid seed to produce F2 progeny seed; d) selecting said F2 plants for having the extra white characteristics of said kohlrabi plant; and e) optionally repeating steps c) and d), wherein either the mother plant or the father plant is a plant as claimed in claim 1 or a progeny plant thereof.

* * * * *